(12) United States Patent
Viellerobe et al.

(10) Patent No.: US 7,285,089 B2
(45) Date of Patent: Oct. 23, 2007

(54) CONFOCAL IMAGING EQUIPMENT IN PARTICULAR FOR ENDOSCOPE

(75) Inventors: Bertrand Viellerobe, Vincennes (FR); Magalie Genet, Paris (FR); Frédéric Berier, Courbevoie (FR); François Lacombe, Chaville (FR); Aymeric Perchant, Paris (FR); Georges Le Goualher, Paris (FR); Sandra Marti, Nanterre (FR); Stéphane Bourriaux, Champs sur Marne (FR)

(73) Assignee: Mauna Kea Technologies, Paris (FR)

( * ) Notice: Subject to any disclaimer, the term of this patent is extended or adjusted under 35 U.S.C. 154(b) by 469 days.

(21) Appl. No.: 10/500,160

(22) PCT Filed: Dec. 20, 2002

(86) PCT No.: PCT/FR02/04481

§ 371 (c)(1),
(2), (4) Date: Jun. 25, 2004

(87) PCT Pub. No.: WO03/056378

PCT Pub. Date: Jul. 10, 2003

(65) Prior Publication Data

US 2005/0078924 A1    Apr. 14, 2005

(30) Foreign Application Priority Data

Dec. 28, 2001    (FR)    .................................. 01 16980

(51) Int. Cl.
*A61B 1/06* (2006.01)
*G02B 26/08* (2006.01)

(52) U.S. Cl. ...................... 600/168; 600/178; 600/182; 600/478; 359/202; 359/205; 385/119

(58) Field of Classification Search ................ 600/160, 600/168, 182, 181, 173, 407, 476, 478; 359/202, 359/205, 455; 385/116, 117, 119
See application file for complete search history.

(56) References Cited

U.S. PATENT DOCUMENTS 4,515,447 A * 5/1985 Weimer et al. ............. 359/388
5,296,700 A * 3/1994 Kumagai .................... 250/216
5,659,642 A * 8/1997 King et al. .................. 385/16

(Continued)

FOREIGN PATENT DOCUMENTS

WO    WO 00/16151    3/2000

(Continued)

*Primary Examiner*—John P. Leubecker
(74) *Attorney, Agent, or Firm*—Young & Thompson

(57) ABSTRACT

Equipment includes an image guide (1) consisting of flexible optical fibers with: on the proximal end side: a source (2), angular scanning elements (3), injection elements (4) in one of the fibers, elements for splitting (5) the illuminating beam and the backscattered signal, elements for spatial filtering (6), elements for detecting (7) the signal, electronic elements (8) for controlling, analyzing and digital processing of the detected signal and display; and on the distal end side: an optical head (9) for focusing the illuminating beam exiting from the illuminated fiber. The scanning elements include a resonant line mirror (M1) and a galvanometric field mirror (M2) with a variable frequency and two afocal optical systems adapted to conjugate the two mirrors (M1, M2) firstly in the field mirror (M2) and the injection elements (4) in the image guide in a second step.

9 Claims, 1 Drawing Sheet

U.S. PATENT DOCUMENTS

| | | |
|---|---|---|
| 5,880,880 A * | 3/1999 | Anderson et al. ........... 359/385 |
| 5,995,867 A | 11/1999 | Zavislan et al. |
| 6,208,886 B1 | 3/2001 | Alfano et al. |
| 6,370,422 B1 * | 4/2002 | Richards-Kortum et al. ..... 600/478 |
| 6,429,968 B1 * | 8/2002 | Carver ....................... 359/385 |
| 6,470,124 B1 | 10/2002 | Le Gargasson et al. |
| 2001/0043383 A1 | 11/2001 | Suga |

FOREIGN PATENT DOCUMENTS

| | | |
|---|---|---|
| WO | WO 01/44854 | 6/2001 |

\* cited by examiner

CONFOCAL IMAGING EQUIPMENT IN PARTICULAR FOR ENDOSCOPE

FIELD OF THE INVENTION

The present invention relates to a confocal imaging equipment in particular for an endoscope and of the type using a flexible optical fibre bundle. The confocal character resides in the use of the same path for illumination and detection, and in the spatial filtering of the signal collected from the subsurface analysis plane.

The fields of application of the invention are in-vivo biological tissue analyses, on humans or animals, external, for example in the field of dermatology, or internal and accessible using the instrument channel of an endoscope into which the flexible optical fibre bundle can be introduced, and also the ex-vivo analysis of tissue samples from biopsies, and the in-vitro analysis of culture in cell biology. Moreover also, the device can serve for the analysis of the interior of a manufactured device.

BACKGROUND OF THE INVENTION

At present the medical fields of gastroenterology, respirology, gynaecology, urology, otorhinolaryngology, dermatology, ophthalmology, cardiology and neurology are concerned.

The use of a flexible optical fibre bundle with a small diameter (several hundred microns) is necessary for coupling with the instrument channel of an endoscope but it can also be advantageous for automatic testing systems in which the optical fibre bundle, with a focusing optical head at its end, is manipulated automatically like a measuring arm on a sample matrix. Moreover, independently of endoscopic use, miniaturization of the optical head is also advantageous for increasing positioning precision and also for minimizing mechanical inertia in automated uses.

More particularly, the equipment according to the invention is of the type comprising a source emitting radiation of a given wavelength producing a parallel illumination beam. This illumination beam is then separated for example by a separating plate in order to split the illumination path and the detection path. It is then deflected angularly in two spatial directions (scanning) by an optomechanical system of mirrors. An optical means then picks up the beam scanned angularly and injects it into an image guide situated in the focal plane of the latter and constituted by an organized bundle of several tens of thousands of flexible optical fibres. Thus, at a given moment, one of the optical fibres of the image guide is injected for a given angular position of the bundle. Over time, the optical fibres constituting the image guide are injected successively, by angular deflection of the beam by means of the mirrors, point-by-point for a given line, and line-by-line in order to constitute the image. The bundle injected into the image guide (if appropriate previously arranged in the instrument channel of an endoscope) is guided, emerges from it and is picked up by an optical means allowing illumination point-by-point of the site which is to be observed. At any moment, the spot illuminating the tissue is backscattered and follows the reverse path of the incident beam. This backscattered flux is then reinjected into the image guide, emerges from it, reaches the scanning system, is then returned on the detection pathway by means of the separating plate, then focussed in a filtering hole. It is then detected for example by a photomultiplier or an avalanche photodiode. The signal originating from the photodetector is then integrated, then digitized in order to be displayed on a screen.

A device of this type is described in particular in International Patent Application WO 00/16151.

In the case of the analysis of a biological tissue, the difficulties that are encountered are linked to the low ratio of useful backscattered signal to parasitic signal, which, in order for the image produced to be acceptable, requires a quality of illumination beam which is the best possible and preserved throughout the optical path, in particular regarding the quality of the wave front and the spatial distribution of the focal spot intensity which must be as close as possible to the diameter of a fibre core. On the side of the proximal end of the image guide, the degradation of the illumination beam with respect to both energy and space is in particular due to the parasitic reflections occurring at the image guide input and to optical transmission faults at the scanning and injection systems (field deformation, wave front error).

In International Patent Application WO 00/16151 mentioned above, the scanning system comprises optomechanical resonating and/or galvanometric mirrors and the system for injecting into the image guide comprises a focusing lens L4 or microscope objective.

OBJECT OF THE INVENTION

The present invention has the aim of proposing an equipment with an improved quality of the illumination beam at the image guide input and as a result an image quality also improved. It also has the aim of proposing a solution, which is low-cost, simple to implement, and which can be miniaturized and produced industrially.

SUMMARY OF THE INVENTION

It proposes a confocal imaging equipment in particular for an endoscope comprising an image guide constituted by flexible optical fibres with:

on the side of the proximal end of the image guide: a source producing an illumination beam, means for angular scanning of said beam, means for injecting the beam deflected alternately into one of the fibres of the image guide, means for separating the illumination beam and the backscattered signal, means for spatial filtering, means for detecting said signal, electronic means for controlling, analyzing and digital processing of the detected signal and for display; and on the side of the distal end of the image guide: an optical head adapted for focusing the illumination beam coming out of the illuminated fibre.

The invention is characterized in that the means for angular scanning comprise a resonating line mirror and a galvanometric frame mirror with a variable frequency and two afocal optical systems adapted to conjugate first the two mirrors then to conjugate the frame mirror and the means for injection into the image guide, each optical system respecting the initial wave front quality (WFE) and having a spatial distribution of the focal spot intensity (PSF) equal to the diameter of a fibre core.

Thanks to these optical means, it is possible to guarantee a quality of the illumination beam and a homogeneous and optimal level of coupling fibre by fibre.

Each optical system can comprise either a set of standard lenses making it possible to carry out the scanning and the injection into the image guide coupled with custom-made additional lenses having the function of correcting the residual aberrations of standard lenses, or a set of custom-made lenses of very good quality.

According to a particular example, an afocal optical system comprises four lenses, a corrective doublet of which being placed symmetrically relative to the image plane makes it possible to correct the curvature of field and minimize the wave front error.

In order to further minimize the residual aberrations, the means for injection into the image guide comprises a set of lenses for converting the angular scanning of the illumination beam to a translational scanning of the image guide which comprises upstream a doublet adapted to correct the residual curvature of field of said set of lenses.

Advantageously according to the invention, the electronic means for controlling, analyzing and digital processing of the detected signal and display means comprise a synchronization card adapted in particular for controlling in a synchronized manner the movement of the line and frame mirrors and adapted to know at any moment the position of the illumination beam scanned.

BRIEF DESCRIPTION OF THE DRAWING

The present invention will be better understood and other advantages will become evident in light of the description which follows of an embodiment, which description refers to FIG. 1 in which an equipment according to said embodiment is represented diagrammatically.

DETAILED DESCRIPTION OF THE INVENTION

Figure 1:
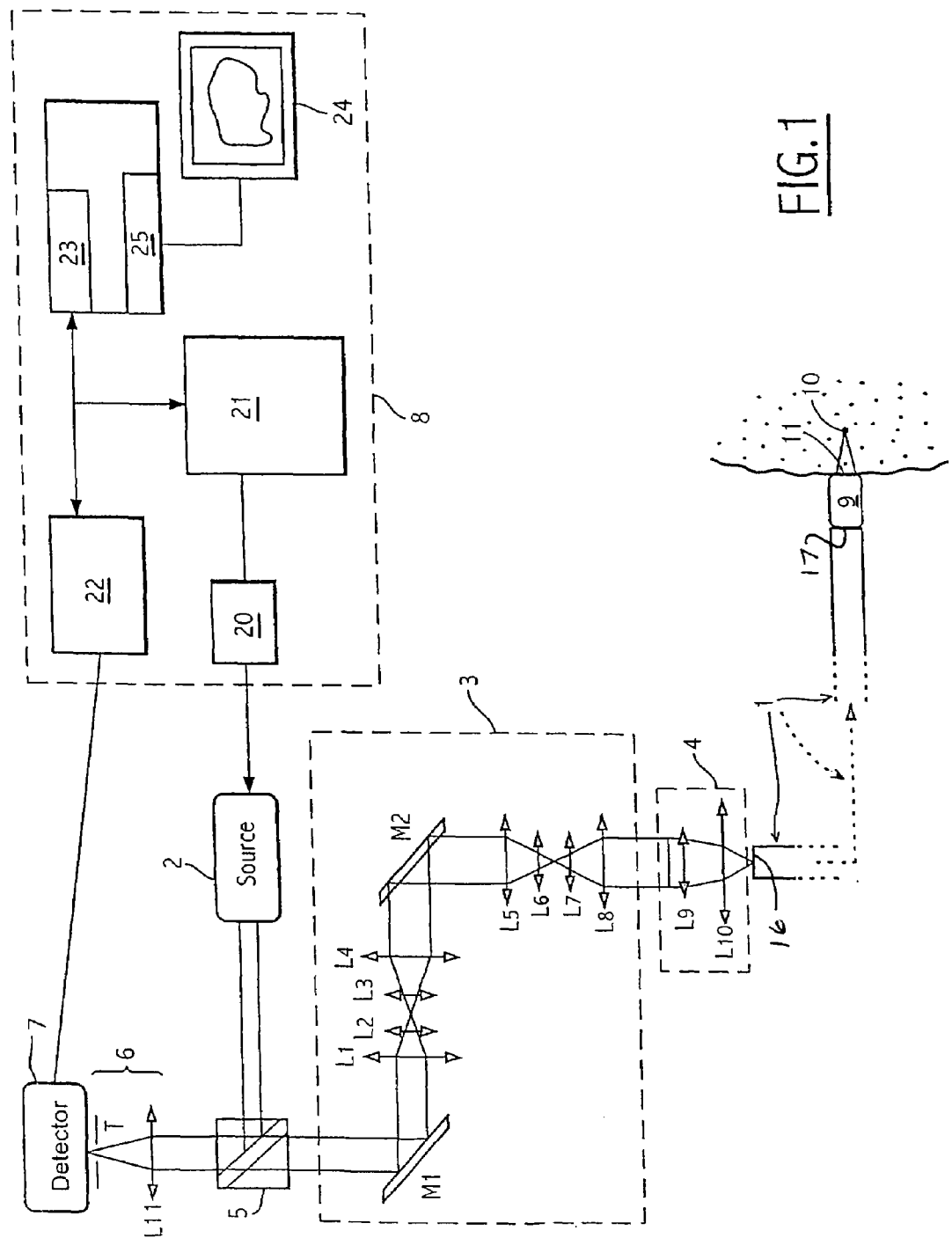

In FIG. 1, an equipment is proposed for producing an image of a site situated at a given depth in a plan P of section XY perpendicular to the optical axis, said equipment comprising an image guide 1 constituted by several tens of thousands of flexible optical fibres with:

on the side of the proximal end of the image guide 1: a source 2 producing an illumination beam, means for angular scanning 3 of said beam, means for injecting 4 the beam deflected alternately into one of the fibres of the image guide 1, means for separating 5 the illumination beam and the backscattered signal, means for spatial filtering 6, means of detecting 7 said signal, electronic means 8 for controlling, analyzing and digital processing of the detected signal and for displaying; and on the side of the distal end of the image guide 1: an optical head 9 adapted for focusing the illumination beam leaving the illuminated fibre of the image guide into a focussed point 10 in the plane P under the contact zone 11 of the optical head 9.

All these means are described hereafter in detail.

The image guide 1 allows access to the subsurface analysis zone by transporting the source 2. If it is intended, with the optical head 9, to be inserted into the instrument channel of the endoscope, it must have dimensions which are compatible (a few millimetres in diameter in accordance with clinical use). It is constituted by an organized bundle of flexible optical fibres surrounded by a sheath. Any guide having enough fibres and a small inter-core spacing can be used in order to obtain a good spatial resolution. By way of example, a guide of Sumitomo® trademark can be used constituted by 30,000 fibres with a core diameter of 2.5 µm and inter-core spacing of 4 µm, or a guide of Fujikura® trademark constituted by 30,000 fibres with a core diameter of 2 µm and inter-core spacing of 3.7 µm. According to the invention, the fibres are illuminated one by one by turns and in an addressed manner, using the scanning means 3 and injection means 4. The useful diameter of the image guide therefore corresponds to the core diameter of an illuminated fibre.

The image guide 1 is equipped at both ends with glass plates 16, 17 thick enough to reject the parasitic reflections outside the filtering means 6 for the reflection occurring at the fibre bundle input, and outside the illuminated optical fibre for the reflection occurring at the image guide output. The glass plates undergo anti-reflection treatment in order to minimize the light reflected.

The source 2 is constituted by a 683 nm laser diode which must have a very good wave front quality, less than or equal to $\lambda/10$. According to the invention, this diode is pulsed in order to split by synchronous detection the useful signal from the parasitic reflection occurring at the image guide 1 input. As a variant, a solid or gas laser can be used, but the choice of wavelength in the 600-800 nm band where absorption into the tissues is lower, is less extensive; moreover, the equivalent power cost is much greater.

The means 5 for separating the illumination beam and the backscattered signal are constituted here by a 50/50 separating cube for adjustment facilities. A 50/50 separating plate can also be used.

The scanning means 3 have the function of reproducing a diode matrix of the same optical quality as the laser diode of the source 2 and which is to be injected fibre by fibre. This requires a combination of non-standard optical means allowing correction of the aberrations that are present in the transport and source duplication system in order to illuminate the signal guide fibre by fibre. The scanning system is constituted by two mirrors M1 and M2 and two optical systems. The mirror M1 is a "line" mirror resonating at a frequency of 4 kHz and the mirror M2 a galvanometric "frame" mirror with a variable frequency between 0 and 300 Hz. Each optical system is constituted by four lenses, respectively L1-L4 and L5-L8, able to conjugate first the two mirrors, then to conjugate the mirror M2 and the image guide input. These optical systems should not have aberrations which could:

widen the spatial distribution of the focal spot intensity (PSF: Point Spread Function) after the injection means 4 and thus degrade the coupling in the image guide 1;

propagate the flux in the sheath of the image guide 1 which would degrade the PSF at the end of the guide and therefore would degrade the image resolution.

The lenses L2-L3 and L6-L7 are identical correcting doublets placed symmetrically relative to the image plane. This allows homogenization of the injection into the image guide by correcting the curvature of field and by minimizing the wave front error due to the use of off-axis afocal systems (L1-L4 and L5-L8).

The injection means 4: These must have the minimum number of aberrations and should not degrade the quality of the wave front in order to produce a focal spot close to the diffraction limit in order thus to produce an optimal coupling with the addressed fibre (a PSF equal to the diameter of a fibre core). They comprise a custom-made doublet L9 and a standard triplet L10. The doublet L9 allows correction of the residual aberrations of the triplet L10, namely the curvature of field.

The means for spatial filtering 6 comprise a lens L11 and a filtering hole T making it possible to select only the illumination fibre and not the adjacent fibres which can generate a parasitic signal. The size of the filtering hole is such that it corresponds to the diameter of a fibre core, taking into account the magnification of the optical system between the fibre bundle input and the filtering hole.

The optical head 9 comprises several optical means allowing convergence of the beam emerging from the illuminated optical fibre and two glass plates, one being described above at the image guide output and the other a window adapted for coming into contact with the site and producing an index adaptation. The optical means have the following characteristics:

allowing analysis of the tissue at a depth of several tens to several hundreds of microns;

minimizing the aberrations in order to transcribe the PSF at the image guide output on the tissue without magnifying the latter or deforming it;

optimizing the return coupling level in the image guide by optimizing the wave front quality;

if appropriate, dimensions compatible with those of the instrument channel of an endoscope.

The optical means comprise for example a lens system forming a custom-made objective.

The detection means 7 comprise an avalanche photodiode as signal detector which receives the signal continuously, the parasitic signal originating from the two ends of the signal guide being carried back with the same order of magnitude as the useful signal in order not to saturate the detector. The suppression of the parasitic reflection residue at the image guide input is then carried out by digital time filtering.

The electronic means 8 for controlling, analyzing and digital processing of the detected signal and for displaying comprise the following cards:

a modulation card 20 of the laser source. This card allows modulation of the source at a relatively high frequency (of the order of 100 MHz) in order to produce pulses (10 ns$\leq\tau\leq$100 ns) at regular intervals (cycle ratio of the order of 4).

a synchronization card 21 which has the functions:
  of controlling in a synchronized manner the scanning, i.e. the movement of the line mirror M1 and frame mirror M2;
  of knowing at any moment the position of the laser spot thus scanned;
  of synchronizing the emission of the laser source pulses before detection;
  of controlling all the other cards via a microcontroller which can itself be controlled;

a detector card 22 which comprises an analogue circuit which in particular carries out an impedance adaptation and integration, a digital-analogue converter and a programmable logic component (for example an FGPA circuit) which formats the signal;

a digital acquisition card 23 which makes it possible to process a variable-frequency digital data stream and to display it on a screen 24;

a graphics card 25.

The image processing is carried out as follows. The raw information from the detector card is formatted and processed so that it can be visualized then interpreted. The process of acquisition of the images via the image guide constituted by several tens of thousands of optical fibres and by scanning of the latter leads to specificities in the image and appropriate processing.

Two processing groups are provided:
1. The first group is constituted by signal processing processes aimed at calibrating the signal received. It is thus possible to eliminate laser/guide coupling faults inherent of the acquisition process, as well as faults due to certain system noises. The calibration can take different forms depending on the scanning control precision, and its stability over time. These processing processes are essentially mono-dimensional.
2. The second group allows improvement of the interpretation by integrating image processing processes (2D and 2D+time) specific to the opto-mechanical process. These processing processes consist of an image restoration process, followed by a rapid alignment process allowing elimination of the small movements. These processing processes are rapid compared with the time taken for acquisition. These algorithms are entirely automatic and are adapted to the nature of the image.

It goes without saying that embodiment variants are possible in particular as regards the line mirror M1 which can resonate at another frequency, for example 8 kHz, the afocal optical systems which can be entirely custom-made or also could comprise other sets of adapted corrective lenses.

The invention claimed is:

1. Confocal imaging equipment comprising an image guide (1) constituted by flexible optical fibres with:
  on the side of the proximal end of the image guide (1): a source (2) producing an illumination beam, means for angular scanning (3) of said beam, means for injecting (4) the beam deflected alternately into one of the fibres of the image guide (1), means for separating (5) the illumination beam and a backscattered signal, means for spatial filtering (6), means for detecting (7) said backscattered signal, electronic means (8) for controlling, analyzing and digital processing of the detected said backscattered signal and display; and
  on the side of the distal end of the image guide (1): an optical head (9) adapted for focusing the illumination beam leaving the illuminated fibre, characterized in that the means for angular scanning (3) comprise a resonating line mirror (M1) and a galvanometric frame mirror (M2) with a variable frequency and two afocal optical systems adapted for conjugating first the two mirrors (M1, M2) then for conjugating the frame mirror (M2) and the injection means (4) in the image guide, each optical system respecting the initial quality of the wave front (WFE) and having a spatial distribution of the focal spot intensity (PSF) equal to the diameter of a fibre core; and in that an afocal optical system comprises standard lenses and corrective lenses adapted for correcting the residual aberrations of said standard lenses.

2. Equipment according to claim 1, characterized in that the afocal optical systems comprise eight lenses (L1-L4; L5-L8) a corrective doublet (L2, L3; L6, L7) of which is placed symmetrically relative to the image plane allowing correction of the curvature of field and minimization of the wave front error.

3. Equipment according to claim 1, characterized in that the injection means (4) comprise a set of lenses (L10) adapted for converting the angular scanning to translational scanning of the image guide and upstream a doublet (L9) adapted for correcting the residual curvature of field of said set of lenses (L10).

4. Equipment according to claim 3, characterized in that said set of lenses (L10) is a triplet.

5. Equipment according to claim 1, characterized in that it comprises a glass plate (16) arranged at an image guide input intended to reject the parasitic reflections outside the filtering means (6).

6. Equipment according to claim 1, characterized in that it comprises a glass plate (17) arranged at an image guide output intended to reject parasitic reflections outside the illuminated optical fibre.

7. Equipment according to claim 1, characterized in that the line mirror (M1) is a mirror resonating at a frequency of 4 kHz.

8. Equipment according to claim 1, characterized in that the frame mirror (M2) has a variable frequency between 0 and 300 Hz.

9. Equipment according to claim 1, characterized in that the electronic means (8) for controlling, analyzing and digital processing of the detected signal and display comprise a synchronization card (21) adapted in particular for controlling in a synchronized manner the movement of the line mirror (M1) and frame mirror (M2) and adapted to know at any moment the position of the scanned illumination beam.

* * * * *